United States Patent [19]
Alt

[11] Patent Number: 4,884,576
[45] Date of Patent: Dec. 5, 1989

[54] SELF ADJUSTING RATE RESPONSIVE CARDIAC PACEMAKER AND METHOD

[76] Inventor: Eckhard Alt, Eichendorffstrasse 52, 8012 Ottobrunn, Fed. Rep. of Germany

[21] Appl. No.: 250,242

[22] Filed: Sep. 28, 1988

[30] Foreign Application Priority Data

Sep. 28, 1987 [DE] Fed. Rep. of Germany ....... 3732640

[51] Int. Cl.⁴ .............................................. A61N 1/36
[52] U.S. Cl. ........................... 128/419 PG; 128/419 P
[58] Field of Search ............. 128/419 PG, 419 P, 736, 128/716, 723, 734, 635, 636, 637

[56] References Cited

U.S. PATENT DOCUMENTS

| | | | |
|---|---|---|---|
| 3,593,718 | 7/1971 | Krasner et al. | 128/419 P |
| 4,535,774 | 8/1985 | Olson | 128/419 PG |
| 4,567,892 | 2/1986 | Plicchi et al. | 128/419 PG |
| 4,576,183 | 3/1986 | Plicchi et al. | 128/419 PG |
| 4,596,251 | 6/1986 | Plicchi et al. | 128/419 PG |
| 4,674,518 | 6/1987 | Salo | 128/695 |
| 4,694,830 | 9/1987 | Lekholm | 128/419 PG |
| 4,697,591 | 10/1987 | Lekholm et al. | 128/419 PG |
| 4,702,253 | 10/1987 | Nappholz et al. | 128/419 PG |
| 4,716,887 | 1/1988 | Koning et al. | 128/635 |
| 4,719,920 | 1/1988 | Alt et al. | 128/736 |
| 4,721,110 | 1/1988 | Lampadius | 128/419 PG |
| 4,722,342 | 2/1988 | Amundson | 128/419 PG |
| 4,730,618 | 3/1988 | Lekholm et al. | 128/419 PG |
| 4,757,815 | 7/1988 | Strandberg et al. | 128/716 |
| 4,790,318 | 12/1988 | Elmqvist et al. | 128/723 |
| 4,791,935 | 12/1988 | Baudino et al. | 128/637 |

OTHER PUBLICATIONS

"Breathing During Exercise", K. Wasserman, *New England Journal of Medicine*, Apr. 6, '78, pp. 780–785.

Primary Examiner—Lee S. Cohen
Assistant Examiner—Scott Getzow
Attorney, Agent, or Firm—Laurence R. Brown; Alfred J. Mangels

[57] ABSTRACT

It has been found from studies of healthy persons and patient's wearing pacemakers that the basic cardiovascular condition and the heart rate response to exercise varies considerably between different individuals. Thus, for effective control the individual differences must be taken into account. It would not be desirable to face the complexity of a pacemaker system that did not automatically adjust to these individual differences because there could not be knowledgeable persons in the field who could establish critical control conditions. This invention thus provides pacemaker methods for automatically establishing operating conditions for proper pacing rate control of a wide range of different individual conditions. Thus on line real time physiologically variable signals from the patient indicative of the patient's basic condition and suitable for pacing rate control are averaged over long and short term intervals and used to develop a pacing control signal. Typically the respiratory rate signal taken from a patient will provide information for adjusting the pacing rate to both the basic condition of the patient and the instanteous conditions encountered such as exercise.

16 Claims, 7 Drawing Sheets

SELF ADJUSTING RATE RESPONSIVE CARDIAC PACEMAKER AND METHOD

This invention relates to my concurrently filed co-pending application Ser. No. 07/250,155 entitled Cardiac and Pulmonary Physiological Analysis via Intracardiac Measurements with a Single Sensor, in that a pacemaker electrode implanted in a patient's heart is commonly used for measurement of cardiac activity and for pacing.

TECHNICAL FIELD

This invention relates to the analysis and processing of instantaneous physiological parameters affecting the heart and more particularly it relates to means and methods of detecting and analyzing both pulmonary and cardiac physiological parameters of a patient with electronic measurements within the heart to derive therefrom information used for automatic pacing rate control of a cardiac pacemaker in accordance with dynamic and historic relationsips to physiological activity of the patient.

BACKGROUND ART

Pacemaker rate control is conventionally derived from control signals obtained from a plurality of measuring elements such as cardiac catheters, special breathing sensors, body temperature sensors, etc. Functional parameters used for the control of the pacing rate are dependent upon a patient's physical condition and dynamically changing exercise parameters. It is desirable therefore to have the pacing rate controlled by information derived from a plurality of physiological parameters of the patient.

Some available publications describe pacing rate control of a pacemaker by measured signals based on the detection of one physiological functional parameter to provide pacing rate control dependent upon pulmonary activity. Thus, in U.S. Pat. No. 4,567,892, G. Plicchi, et. al., Feb. 4, 1986, the respiratory rate is determined from an implanted secondary electrode by an impedance measurement. In U.S. Pat. No. 4,697,591, A. Lekholm, et al., Oct. 6, 1987, the respiratory rate is determined from impedance across the chest cavity by using the can and heart implant electrodes. In U.S. Pat. No.4,596,251, G. Plicchi, et al., June 24, 1986, the respiratory minute volume is measured by impedance changes from at least one electrode located in the chest cavity. Other related respiratory rate controls are effected in U.S. Pat. Nos. 3,593,718, J. L. Krasner et al., July 20, 1971; 4,721,110, M. S. Lampadius, Jan. 26, 1988 and 4,702,253, T. A. Nappholz et al., Oct. 27, 1987. In U.S. Pat. No. 4,576.183 G. Plicchi, et al., Mar. 18, 1986 subcutaneous electrodes in a patient's chest are used to measure impedance for control by a respiratory parameter.

Recently there have also been proposals to control the pacing rate of a cardiac pacemaker from two or more physiological functional parameters. In German Pat. P 36 31 155C, published Mar. 24, 1988, pacing rate is controlled for stable long-term control from the temperature of the venous blood within the heart and from an activity sensor for short-term exercise related activity. The temperature signals can be modulated by the activity signals for an optimal adaptation of the pacing rate to the particular exercise of the patient. Different sensors may be used to check the two functional parameters. The pacemaker control is based on the finding that essentially only parameters such as the blood temperature and activity should be used as absolute values for determining a relationship between these parameters and the pacing rate, whereas other physiological functional parameters are merely relative parameters, which at least impede stable long-term control of the pacemaker. U.S. Pat. No. 4,722,342, D. Amundson, Feb. 2, 1988 provides a plurality of different body activity sensors to derive variable pacer controls for body activity. Respiratory control of a pacemaker pulse rate with a respiratory signal derived from analyzing the stimulation pulse reaction on the already implanted pacemaker electrode is set forth in U.S. Pat. No. 4,694,830 issued to A. Lekholm Sept. 22, 1987.

The first generation of rate responsive cardiac pacemakers used only one parameter to control the rate of pacing. In U.S. Pat. No. 4,527,568 of A. Rickards, July 9, 1985, the change of QT interval with exercise is proposed for rate control. With that parameter it is not possible to establish an absolute relation between QT interval and heart rate. Therefore, a rate responsive pacemaker can use this parameter for rate control only if relative changes of the parameter are applied to a self-established relative baseline value. More advanced concepts of rate control using the QT interval and adjusting the slope automatically on the measured QT interval are disclosed in Vitatron Medical: Clinical Evaluation Report Model 919, Aug. 1988, Velp. Even though this represents an advanced concept, it suffers from considerable drawbacks. Since the QT interval as the control parameter depends on paced heart beats, correct adjustments are not achievable in those patients that feature intrinsic heart beats. This makes possible the automatic gain setting only in those patients that depend on continuously paced heart beats. As an in built 24 hour clock is additionally needed to define night time (assumed to be the resting time) for these measurements, difficulties arise with those patients that are active at night or that travel with differences in local time.

As far as the relativity of a parameter is concerned, the same holds true for several other parameters that have been proposed for control as in U.S. Pat. Nos. 4,535,774, W. H. Olson, Aug. 20, 1985; 4,674,518, R. W. Salo, June 23, 1987; and 4,566,456, G. Koning, et al., Jan. 28, 1986. Both techinical limitations and underlying human physiology prevents satisfactory operation of such systems. Use of blood temperature for control of rate responsive cardiac pacing is proposed in U.S. Pat. Nos. 4,436,092, Mar. 13, 1984; 4,543,954, Oct. 1, 1985; and 4,719,920, Jan. 19, 1988. The time delays imposed by temperature changes make real time response to sensed physiological parameters in a patient more difficult.

The prior art in general has assumed that an absolute relation between a physiological parameter and the pacing rate should fit different metabolic conditions of the patient. However the prior art does not custom fit or tailor the pacing rate with a plurality of sensed physiological parameters to offset individual patient response to variable conditions such as exercise, nor adjust the pacemaker rate response to exercise in accordance with the different basic conditions of the various individual patients.

Furthermore such prior pacemaker controls are generally deficient in their controls of pacing in response to a patient's condition because of measurement errors attributed to interference between pacing pulses and electric sensor pulses, or to errors induced by improper ventilation signals derived from a plurality of sensor electrodes and sensor electrodes located where false signals are given from body motion, coughing or the like.

None of the prior art therefore could reliably provide dynamic adjustments of the pacing rate to fit the characteristic unique needs of an individual patient, particularly since there is no uniformity of response of patients to different work loads, for example.

Therefore, it is an object of this invention to provide more reliable determination of a patient's individual physiological parameters and basic condition to use them for automatically adjusting the pacing pulses to an individually tailored optimum rate for both rest and exercise.

A further object of this invention is to provide control of pacing rates tailored to respond to individual exercise and respiratory characteristics of a patient.

SUMMARY OF THE INVENTION

The present invention affords automatic adjustment of pacing rates in response to dynamically sensed pulmonary and cardiac parameters of the patient and other known individual characteristics of a particular patient. Applicant's investigation of more 100 pacemaker patient's has established dramatic differences in correlations between respiratory rate and heart rate with work loads of different individuals. Thus to meet the needs of a realistic set of patients, it becomes necessary to establish a self-adjusting relationship of respiratory rates to pacing rates. Other parameters relating to the history, aging, disease, etc. of the patient may be programmed into the pacemaker to further optimize the pacing rate selection process.

Accordingly an algorithm for pacing control is developed as related to personal characteristics of the patient both historically and dynamically as sensed to determine physiological activity preferably related to instantaneous real time cardiac and pulmonary response to exercise, rest, and other conditions encountered by the patient.

Implicit in the selected pacing rate is the reliability of the sensed data to eliminate extraneous noise or false signals, and to employ measurement techniques accurately representing the particular physiological demands on an individual patient. Also feasiblity of adoption is facilitated by preferably using only the necessarily pacing electrode implanted in the heart as the dynamic sensor element.

This single sensor located within the right heart is made operable to measure in essence different blood conditions by way of the single intracardiac functiional parameter, namely impedance. Both intrathoracic pressure fluctuations correlating with the patient's breathing and the activity coming from the heart itself thus are detected reliably.

Investigations by applicant correlate breathing and intrathoracic pressure fluctuations with the impedance measurement of blood in the heart. Thus pacing is controlled by reliably produced physiological varations of the patient from which are derivied control algorithm input data dependent upon such parameters as the rate and depth of respiration, contractility of the mycoardium, stroke volume, etc. Great advantages are obtained in control of a cardiac pacemaker in response to these detected signals.

The respiratory rate corresponding to the frequency of the low-frequency periodic signal band is used in three different ways to achieve an optimum rate control of a patient's heartbeat. First is formulation of an absolute or base value (which may be conditioned for the personal characteristics of an individual patient) for a predetermined relation between the respiratory rate and the pacing rate. The second is use of the respiratory rate seen with physical exercise to achieve an increase in heart rate according to the relation of the instantanious patient condition compared to the basic condition. The third is to make the relation between pacing rate and exercise response of physiological parameters an automatic function of the constantly monitored and constantly readjusted basic cardiopulmonary condition.

The basic characteristic of the pulmonary signal additionally can be converted into other relatively varying respiratory functional parameter subsignals determined from the low frequency band signals. Of significance in the pulmonary signals are the tidal volume and the respiration rate subsignals. Thus the heartbeat rate in a pacemaker is optimized with respect to the pulmonary activity generated in real time.

The invention also optimizes a cardiac pacemaker system in response to changes of metabolic demands caused from exercise and thus historically stores and determines those parameters best suited for cardiac pacing control in accordance with a particular patient's characteristic exercise induced physiological dynamics and history. Accordingly a microprocessor is programmed with predisclosed patient characteristics relevant to the pacing rate to determine a tailored base line characteristic which is modulated by dynamically produced pertinent data sensed dynamically in instantaneous real time.

BRIEF DESRCIPTION OF THE DRAWINGS

The invention shall be explained in more detail in an exemplary embodiment in connection with a cardiac pacemaker with reference to the accompanying drawings, in which.

Figure 1:
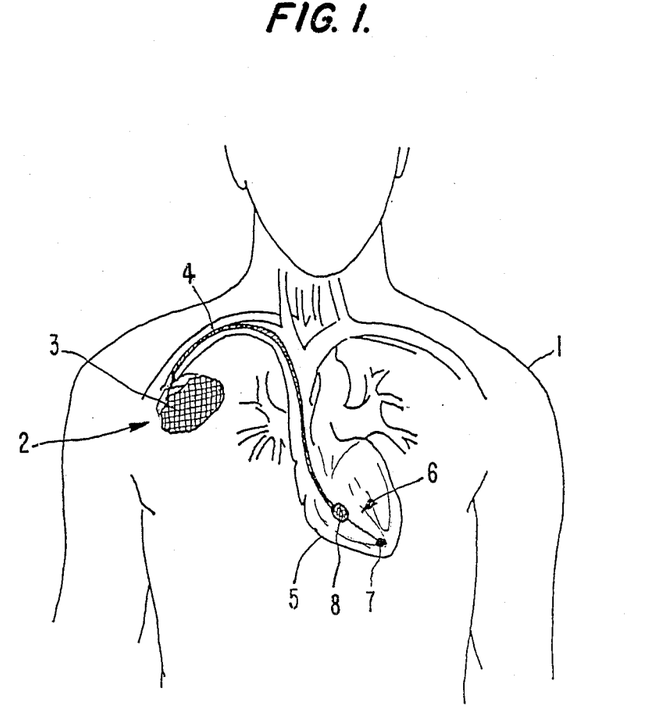
FIG. 1 shows a schematic view of an inventive cardiac pacemaker electrode system implanted in a patient's right heart.

THE PREFERRED EMBODIMENTS OF THE INVENTION:

FIG. 1 shows a cardiac pacemaker 2 implanted in a patient 1, comprising a can 3 from which a probe 4 leads via a vein into heart 5. Probe 4 is designed at its front end located in the ventricle as a sensor-pacer electrode 6 having a first pole 7 located at the tip of the probe 4 and a second pole 8 located more proximally. As seen from FIG. 2, electrical lines 9 and 10 within probe 4 connect the two spaced poles 7 and 8 located within the right ventricle with a control and pacing circuit 11 disposed in can 3.

Figure 2:
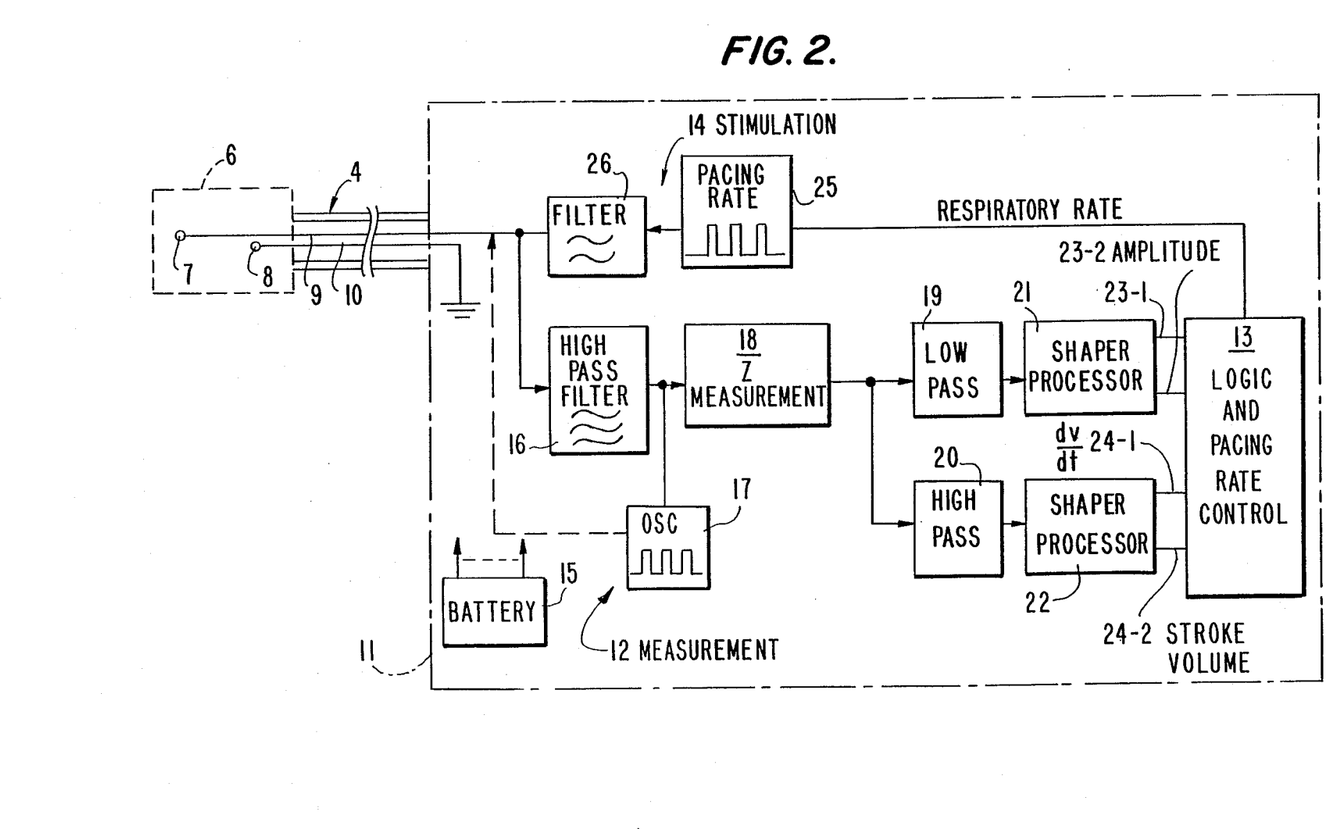
FIGS. 2 and 3 show in block diagram form the electronic diagnosis and control system of a preferred embodiment afforded by this invention, FIGS. 4A, B, C and D are charts relating the respiratory rate of different types of patients while exercising at different work loads.

The block diagram control circuit 11 has functionally defined control circuit elements which can be embodied into an itegrated circuit along with associated microprocessing means and appropriate software. The control circuit comprises generally a measurement section 12, a logic section 13 and a stimulation section 14. Energy is supplied by battery 15.

One line 10 from detector electrode pole 8 is connected to ground potential. The other detector signal line 9 is coupled to the signal measurement section 12 by high pass filter 16. An oscillator 17 provides alternating current for impedance measurement with a frequency between approximately 1 kHz and 100 kHz. This measurement signal is of such low comparative signal strength that it does not interfere with pacer stimulation at the commonly shared electrode 6. A low current amplitude in the range of a few microamperes, or alternatively single pulses of 0.01 msec duration and amplitude of less than a milliampere, also reduces battery load. The current signal of oscillator 17 is shown applied to the measuring-stimulus electrode 6 by way of the dotted lead.

The resistance (or impedance) within the heart between the electrode 6 poles 7 and 8, as defined by Ohm's law, is determined in the impedance measuring means 18 following high-pass filter 16 which passes the signal at the oscillator 17 frequency, which is significantly higher than the pacing rate, which is thereby eliminated so that it can have no interfering effect on the impedance measurements. The resulting raw sensor signal varying dynamically in impedance is fed on one hand to a low-pass filter circuit 19 and on the other hand to a high-pass filter circuit 20, which splits the impedance modulated signal into lower and higher frequency portions. Thus, low-pass circuit 19 passes signals associated with the patient's lower respiratory rate, whereas high-pass circuit 20 passes signals associated with the patient's higher-rate cardiac activity. Since the heart rate is generally four to five times higher than the respiratory rate, these respiratory or pulmonary and cardiac signals can be separated with state of the art filters.

The output signals of low-pass and high-pass circuits 19, 20 are each fed to a respective signal shaping-processor circuits 21, 22 for preevaluation, e.g. averaging, amplitude and frequency analysis, determination of the derivative in time and subsequent integration, or the like. An output line 23-1 of low-pass circuit 21 then provides a signal associated with the respiratory rate and corresponding to the periodic frequency of the low-frequency signal. The further output line 23-2 provides a signal associated with the depth of respiration and corresponding to the amplitude of the low-frequency signal. An output line 24-1 of high-pass circuit 22 provides a signal associated with the contractility of the heart and corresponding to the derivative in time (dV/dt) of the high-pass filtered stroke volume (V) impedance signal, i.e., the rate of change in time of the systolic stroke volume. A further output line 24-2 provides a signal associated with the stroke volume of the heart and corresponding to the amplitude of the high-passed impedance signal.

All output lines 23, 24 are connected to logic and pacing rate control circuits 13, which includes a microprocessor to calculate on the basis of available signals, an otimum pacing rate related to the exercise of the pacemaker wearer. This pacing rate is fed to a pulse generator 25 in stimulation signal section 14, which provides corresponding stimulation pulses to the bipolar electrode 6 via a low pass filter 26 transmitting only the basic pacing pulses. The frequencies of measuring channel 12 and stimulation channel 14 are separated by filters 16 and 26 so that the signals in one channel do not interfere and impair the functioning of the other channel. In this manner the bi-polar electrode 6 can be used both as a measuring electrode and as a stimulation electrode.

Figure 3:
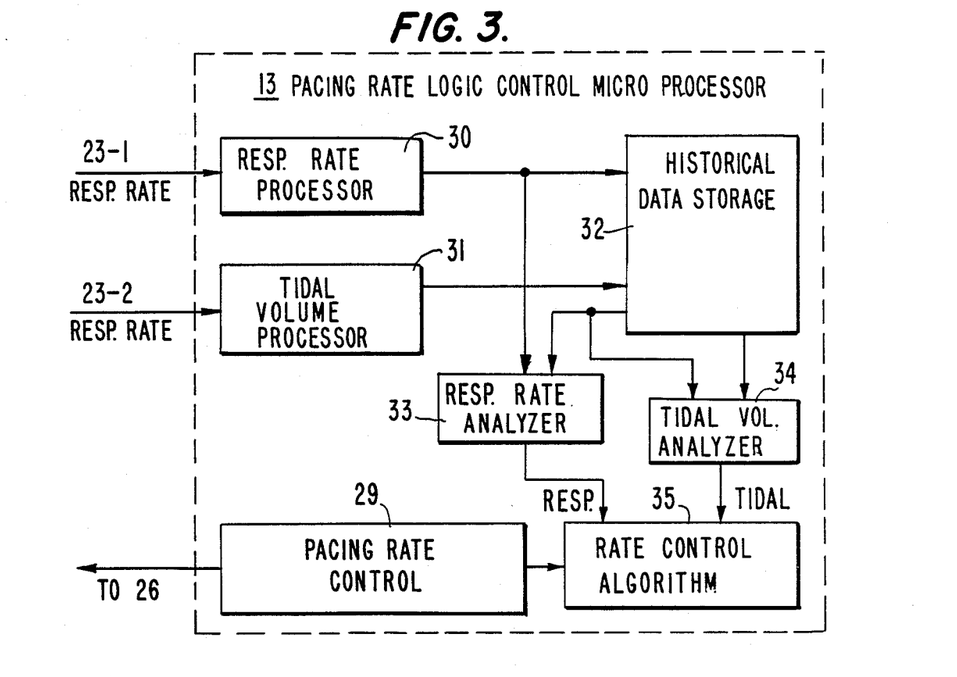

Further operation of the logic pacing rate control circuit 13, as afforded by this invention in connection with pulmonary activity analysis, is set forth in FIG. 3. Thus, the lower frequency pulmonary signals at 23-1 and 23-2 respectively relating to respiratory rate and respiratory amplitude are processed by respective circuits 30, 31, such as by digitalizing to produce signals for use in the microprocessor contained in logic control section 13. Historical data is then stored at store 32 over a predetermined storage period to make available previously monitored signals.

Analyzers 33 and 34 then respectively process the respiratory rate and tidal volume current and corresponding historic signals taken from store 32 to provide control signal data corresponding with a control algorithm determined for optimum pacing controls from those respective signals. These respective control signals are then combined into a master control algorithm optomized for pacing rate control in block 35 for use by the pacing rate control circuit that sends heart stimulation signals via pacing stimulation section 25, filter 26 and probe 4 to the implanted stimulation electrode based upon both current sensed physiological reactions of the patient and past data from recently encountered physiological reactions sensed over a predetermined time period such as the last hours.

The following waveform charts and general discussions will make evident appropriate data and operating methods provided by this inevntion from which microprocessor programs for the particular microprocessor of control logic system 13 are formulated for producing pacing control algorithms. Provisions are made, as hereinafter set forth for optimal control of the pacing rate in accordance with policy selctions made for individual patient requirements with appropriate medical advice. The technical way of processing impedance data has been disclosed in the past in such pacing systems as shown for example in Plicchi et al., 4,567,892, supra; Koning, et al., 4,566,456, supra; or Amundson, 4,722,342, supra may be modified to operate in accordance with the principles of this invention by those skilled in the cardiac pacer arts.

On the basis of studies applicant has conducted in healthy persons and in many particular patients, breaths determined in terms of impedance within the heart can be correctly associated with real breaths in more than 95% of all breathing actions, so that the determined respiratory rate constitutes an absolute value to be detected very reliably over a long time. Within a control algorithm the absolutely measured respiratory rate therefore constitutes the reference value and as an absolute value the basis of control. According to measurements performed by us on more than 100 pacemaker patients, the respiratory rate shows a relation to heart rate characterized by an S-shaped curve, similar to that reported by K. Wasserman, The New England Journal of Medicine, p780ff, Apr. 6, 1978 in an article entitled "Breathing during Exercise". In the range of low respiratory rates the ratio of respiratory rate to heart rate is lower, and in the range of higher respiratory rates there is also a flatter relation between the respiratory rate increase and heart rate increases. This is due to the fact that under high-intensity stresses breathing increases overproportionately to oxygen absorption due to other compensatory mechanisms within the cardiopulmonary system taking over. On the basis of these results confirmed by us, a relation is proposed which provides a different correlation of respiratory rate to heart rate in accordance with the respiratory rate for use in an on-line pacemaker control method afforded by this invention.

This association of respiratory rate with heart rate constitutes the basic framework within a control algorithm. Furthermore, the respiratory rate is modified in its relation to the heart rate by additional cardiac and pulmonary influencing factors. Thus, an increase in contractility leads to a higher heart rate at the same respiratory rate. Similarly, an increase in the relatively determined stroke volume and the tidal volume leads to an increase in the heart rate at the same respiratory rate. In the converse case it is also true that a reduction in the aforesaid parameters leads to a drop in the heart rate while the respiratory rate is constant. An essential point of the invention, however, is that the long term average respiratory rate indicating the patient's basic condition, as an absolute value, constitutes the particular reference value within the control by other relatively varying values. One of these relatively changing values is the instantaneous respiratory rate which is compared as a relative change to the long term average respiratory rate indicating the individual stress of the instantaneous metabolic situation of the individual patient.

Since the tidal volume, stroke volume and contractility determined via the rate of change of intracardiac impedance per unit of time only constitute relative values, only changes relative to a basic value continuously redefined by averaging gain entry to the rate regulation. This means that a longer existing constant increase in the relative measured value of stroke volume, contractility or tidal volume is evaluated accordingly as the new basic value after a freely selectable predetermined time interval.

Thus, changes of intra-cardiac impedance due to external factors, for example electrolyte changes, changes of the hematocrit, changes of temperature or changes of the ventricle configuration (patient's position), and infarctions or influence on the contractile pattern of the myocardium by medication (water tablets), can be take into consideration accordingly. This corresponds to the measuring data obtained in our tests, that stroke volume, tidal volume and contractility are only detected as relatively varying values and are only suitable to a limited extent as sole rate-determining parameters for a rate adaptive pacemaker therapy. However, they can be usefully combined with an absolute measured value detected stably over a long time, such as the respiratory rate. Due to their potential negative feedback with the pacing rate (return of measured value, e.g. stroke volume, in case of inadequate excessively fast pacing and thus return of the rate), the parameters to be detected relatively are very suitable for optimizing the pacing rate by feedback.

With respect to the exercise dynamics both short term and long term history is of importance for variation of pacing rates. Also it is known that the physical condition of the patient needs to be considered for improved dynamic control of pacing. FIG. 4 will illustrate the particular need to provide control information specifically tailored for individual patients. This invention produces from dynamically sensed signals information relating to the individual patient's characteristic patterens of physiological cardiac and pulmonary response that will produce better pacing controls.

Figure 4A:
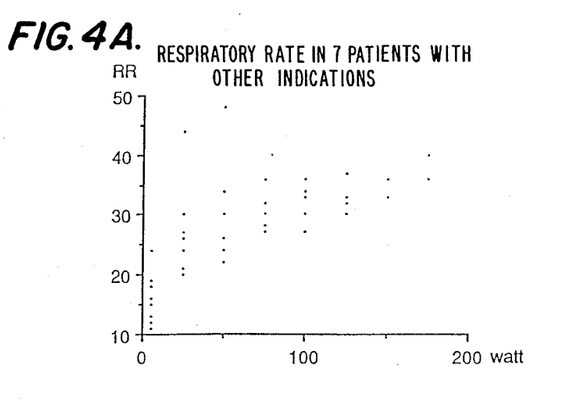
Figure 4B:
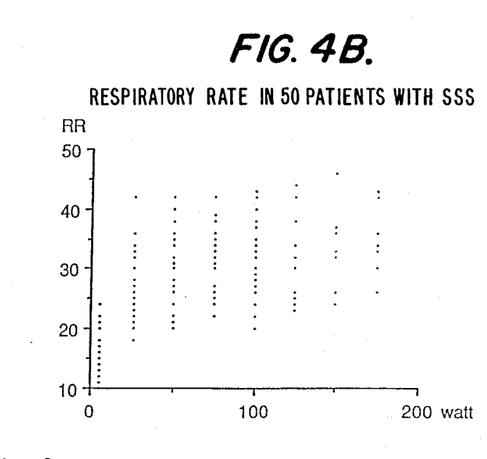
Figure 4C:
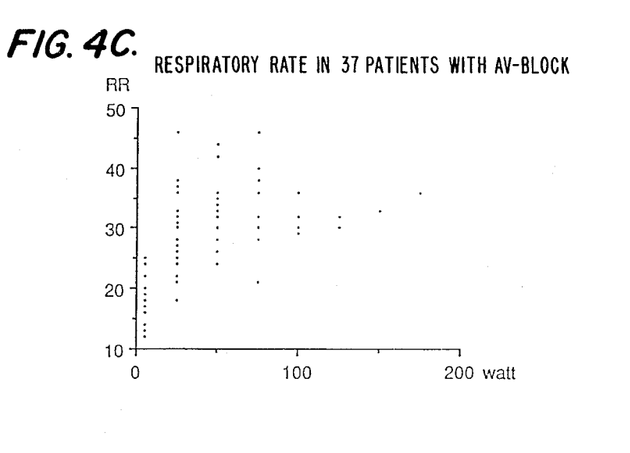
Figure 4D:
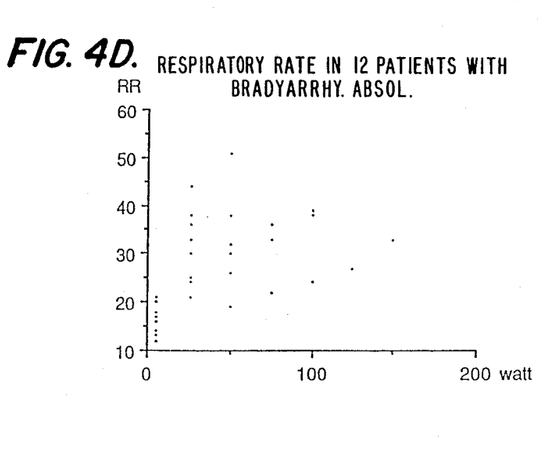

In investigations performed by applicant in more than 100 pacemaker patients, as set forth in FIGS. 4A to D, it is demonstrated that the relation between respiratory rate with different levels of exercise shows dramatic differences for different individuals. Respiratory rates at rest varied between about 11 and 24 for different individuals, as seen from the zero level work load dots on the various charts showing different patient conditions. FIG. 4A is the most representative for the "normal" individual featuring those pacemaker candidates that only intermittently need pacemakers. FIGS. 4B to D feature respiratory rates in patients that received pacemakers for the different identified underlying disorders. In the various views of FIGS. 4A to D it is seen that a respiratory rate of 24 breaths/minute was found in some patients already at rest while in other patients at work loads from 25 to 150 watts a respiratory rate of 24 breaths per minute was present depending upon the condition and individuality of the patient. Therefore to link pacing to a respiratory rate level only on a pregiven fixed basis would be inappropriate in many cases.

This invention therefore contemplates a self adjusting relationship between respiratory rate and heart considering the patient's underlying condition.

It was also found in these studies that those patients exhibiting a high respiratory rate with exercise also exhibit a high respiratory rate at rest. Another finding in non pacemaker bearing patients was that the higher respiratory rate at rest was associated with higher heart rates at rest. Additionally it was determined that the relationship of a change of respiratory rate to a change in heart rate under exercise differs considerably from the same relationship under resting conditions. This is especially so if the differences in the relationship at rest of different individuals are considered.

Thus this invention applies different relationships of the respiratory rate and pacing rate for rest and exercise conditions to patients depending upon their individual characteristic physical condition.

Thus control of pacing is made dependent upon a long-term average of respiratory rate as the base level, and by adjusting the pacing rate in response to the respiratory rate. For example, if a patient exhibits an average respiratory rate of only eight breaths per minute, indicating a well trained or healthy person, his basic pacing rate would be as an example 56 beats per minute An average pacemaker patient exhibiting a resting respiratory rate of 16 breaths per minute would have a basic pacing rate of 72 beats per minute. An average respiratory rate of 22 breaths per minute indicating an impaired cardiopulmonary condition would result in a basic pacing rate of 84 beats per minute for example. A relationship with a change of respiratory rate at rest of one breath per minute to a change of pacing rate of two beats per minute corresponds well to the behavior found in normal non pacemaker patients. But with exercise, a different relation of a change of respiratory rate of one breath per minute to a change of pacing rate of three to six beats per minute was found to be adequate.

Further on it was found that patients who started exercise at already relatively elevated levels of resting respiratory rate showed a steeper increase of heart rate with the same level of exercise compared to patients who started at lower resting rates. The slope of the relationship between an increase of respiratory rate with exercise to the increase in pacing rate is thus controlled in accordance with this invention automatically according to the basic physical condition of the individual patient in accordance with dynamically sensed data. Thus, the long term average of respiratory rate is a critical control element for pacing rate An algorithmic control function then may calculate a long term average of the value of respiratory rate over several hours, at least over a time period exceeding the longest continuously performed exercise by a factor of two, and to link heart pacing rate to this value by using a slope of one breath per minute to two beats per minute for example.

The actual respiratory rate is determined out of a short term average of the last four to eight respiratory cycles. The difference between long term and short term average values is used to modify the resting pacing rate base line. Here a typical slope of one breath per minute to three to six beats per minute rate increase is applied. This slope can be a function of the long-term average resting respiratory rate.

Other parameters that are linked to heart rate, in the manner hereafter discussed for example, are used for pacing rate control. These are preferably also taken as a difference between the long term and short term averages of the individual parameter multiplied by a predetermined slope to modify the base pacing rate. Automatic ramping is achieved by selecting the durations of the time constants of the long and short term averages. All these control functions are readily programmed in a microprocessor for automated control of the pacing rate. For cardiac parameters for example a ramping time of two to twenty five minutes is appropriate considering their only relative value for rate control following a possible change in their absolute values without change in actual condition and pacing rate.

Figure 5:
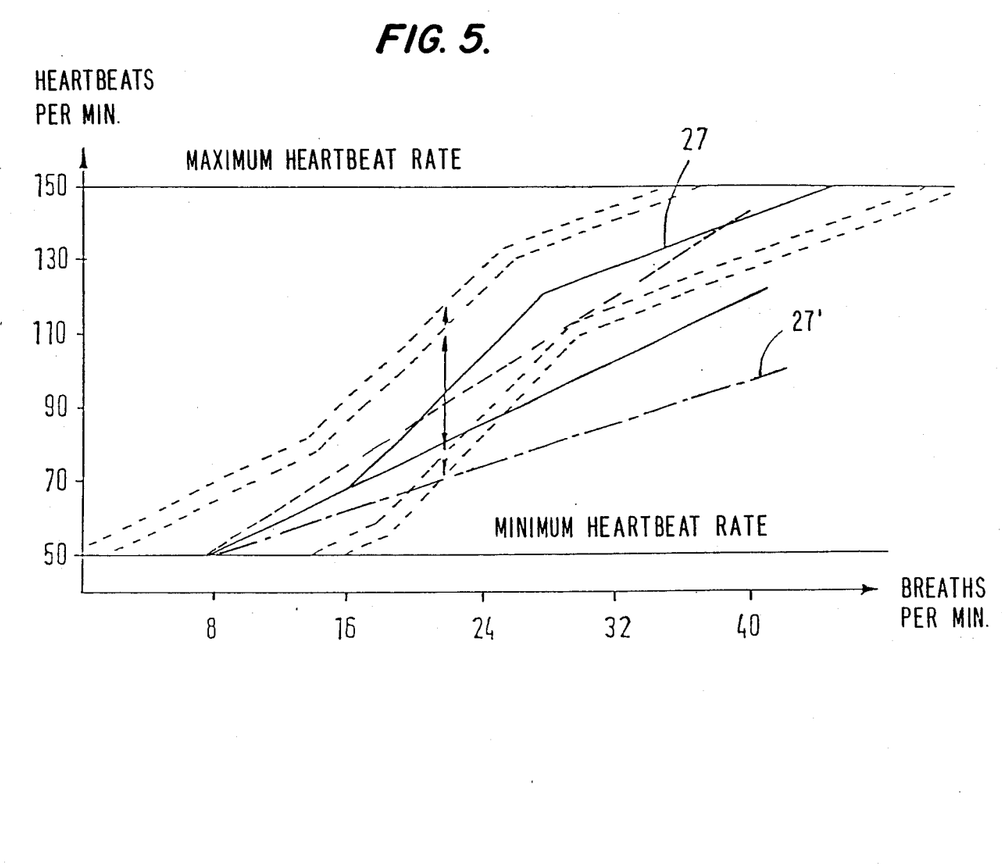
FIG. 5 is a chart showing interrelated human breathing-heartbeat rate curves and the modulation of a predetermined relationship between respiratory rate and heart rate of a pacemaker by other parameters than the respiratory rate.

To control the pacing rate in accordance with exercise of a pacemaker wearer, a basic control characteristic 27 shown in FIG. 5 is used. This depends upon the sensed variables to set a control relationship depending upon the respiratory rate and the heartbeat rate appearing at the sensor electrode in the heart. The basic characteristic 27 is linearized within three sections of varying slopes. A first slope is for heartbeat rates ranging between about 50 to 70 beats per minute with corresponding long term averaged respiratory rates between about eight to sixteen breaths per minute. Similarly, a second slope is for heartbeat rates ranging between about 70 to 120 beats per minute with a corresponding sixteen to about 28 breaths per minute and a third slope is for heartbeat rates ranging between about 120 to 150 beats per minute with a corresponding rspiratory rate between about 28 and 44 breaths per minute. The upper limit of the heartbeat rates is fixed at 150 beats per minute and the lower limit at 50 beats per minute. The curve and steepness of this characteristic can be adapted to the patient's individual needs, and this can be done non-invasively after implantation. For example, if it seems to be appropriate according to the profile of the individual patient an alternative relation of the long term average of the respiratory rate to heart rate ratio as shown by the additional dotted lines 27' of more steep or more flat slope showing only one principal relationship of long term averaged respiratory rate to basic heart rate might be selected alternatively.

However, the actual pacing rate is not determined by this basic characteristic 27 or 27' alone. The latter can be modulated in accordance with a plurality of functional parameters determined in measuing channel 12. In the most simple case this shifts the characteristic parallel to the ordinate, i.e., the heartbeat rate, as indicated by the dotted characteristics in FIG. 5. The other functional parameters determined in the measuring channel, which are present on lines 23-2, 24-1 and 24-2 of FIG. 2 then constantly redefine the particular base line or initial value for the basic characteristic, so to speak.

It is seen that the control of pacing rate in this preferred embodiment of the invention is dependent upon the dynamic respiratory signal component respiratory rate or breaths per minute. The basic control characteristic is developed automatically in accordance with this invention to suit the individual characteristics of a wide range of pacemaker wearers. Thus the on line real time response to the pulmonary system of the patient is represented by the low pass filtered signals at shaper processor 21 of FIG. 2, which correspond to the dynamic respiratory activity of the patient. The basic pacing rate control relationship is expressed in FIG. 5 as the control characteristic or base line 27 which is developed from a long term average of the respiratory rate of the patient representative therefore of the patient's basic cardiopulmonary condition. It should be clearly understood that this basic condition can vary with various influences such as pneumonia, fever, pulmonary embolism and the like, and that an appropriate adjustment of pacing rate according to the basic relationship of for example one breath per minute difference effects a change in pacing rate of two beats per minute. In order to respond also to those changes, but not to comprise the effectiveness of respiratory control with the exercise, the average of the breathing rate over about eight to sixteen hours is taken as the long term average. This individualizes the control factor therefore to take into account the variations of the underlying dasic respiratory rates as set forth in FIG. 4. Also it serves to dynamically extend the range between rest and exercise conditions and provide a smooth transition of pacing control under various exercise conditions. Thus, although the primary basic pacing rate relationship of the base line 27 is shown fixed, the instantaneous pacing rate actually varies dynamically with the respiratory rate history averaged over the predetermined period long term average and gets modulated by the acute respiratory rate which is averaged over a short term period such as 4 to 8 respiratory cycles.

Furthermore, to take into account dynamic physiological activity of the patient, such as the start or stop of exercise where pacing rate controls are critical, the base control line 27 is varied dynamically not only by a corresponding short term average of four to eight breaths representative of the patient's instantaneous cardiopulmonary condition but also by other parameters indicating exercise. By varying the basic pacing rate control function 27 as a function of the short term averages or the differences between short and long term average, the master pacing control signal relationship is established, which is used to establish the pacing rate in the pacemaker.

This makes clear that in similar manner the other dynamically measured signals which relate to the pacing rate, such as the tidal volume or amplitude at 23-2 of FIG. 2, of the contractility signal dV/dt at lead 24-1 or the stroke volume signal 24-2 may be used, as well as other exercise activity signals or dynamically sensed physiological activity relating to the pacing rate.

Accordingly, for example, the tidal volume signal may be used as another control medium. Thus the long term average is taken for representing the patient's basic pulmonary condition. Then a short term average of the tidal volume representative of the patient's instantaneous pulmonary condition is taken and used to vary the long term basic tidal volume signal in an appropriate functional relationship to establish a tidal volume control signal, which in turn varies the original pacing control signal to establish a different base control characteristic such as one of the dotted lines in FIG. 5.

The degree or function of variation for any of the sub-control signals is determined by the optimal effect of the corresponding measured dynamic parameter upon pacing rate. it is seen therefore that in this way automatic dynamic adjustment of the pacing rate can be reliably done with reliable dynamic intracardiac impedance measurements, for example, to satisfactorily perform over the various conditions of FIG. 4.

Figure 6:
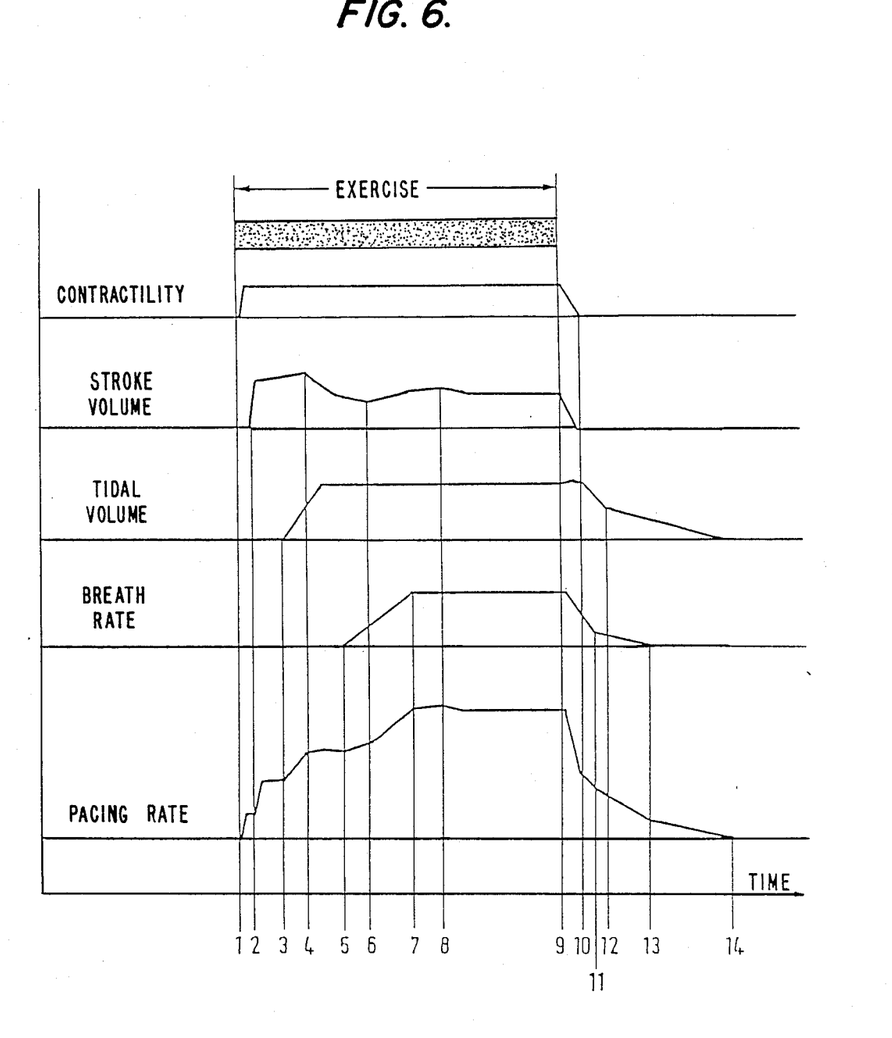
FIG. 6 is a waveform chart of variations in pacing rate in response to various physilogical characteristics as related to an exercise period.

The method of operating the cardiac pacemaker in accordance with this invention is explained further with reference to the dynamic activity shown in FIG. 6. These characteristics may be used to determine the functional relationships between basic and sub-control signals and the pacing rate for automatic pacing as just described.

In this figure the functional parameters, namely: contractility of the heart, stroke volume, tidal volume, instantaneous respiratory rate and pacing rate are recorded over a time period starting before and ending after exercise of the pacemaker wearer. When the wearer is at rest, the pacing rate is determined solely by the absolute basic characteristic 27 in accordance with the long term averaged respiratory rate. When the wearer exercises at time 1, the contractility of the heart first increases, which is indicated by the signal on line 24-1. This increases the pacing rate.

At time 2 the stroke volume also increases, thereby further increasing the pacing rate. The stroke volume becomes approximately constant after a short time, so that the pacing rate from this parameter is also then kept approximately constant. At time 3 the tidal volume increases while the stroke volume and contractility remain essentially constant. The pacing rate is thus increased by the tidal volume until it levels off at time 4, when the stroke volume is slightly decreasing. The drop in stroke volume indicates that the pacing rate has risen to a range in which the stroke volume goes back slightly and finds its new optimum, although the tidal volume is increasing even further. This results in an approximately constant pacing rate from the effect of these two parameters during the time period 4 to 5.

At time 5 the instantaneous respiratory rate also increases so that the working rate of the pacemaker increases following an additional shift of the basic characteristic 27. The increase is relatively moderate, since the stroke volume is still slightly dropping at this time. However, at time 6, the respiratory rate continues to increase while the stroke volume is relatively constant, so that the pacing rate is increased until a constant respiratorry rate occurs at time 7. Contractility, stroke volume and tidal volume are essentially constant at this time. Then between times 7 and 8 the stroke volume increases slightly while the other functional parameters remain constant, thus increasing the pacing rate slightly.

Between times 8 and 9 all functional parameters are approximately constant, so that the pacing rate remains constant. At time 9 the exercise ceases, causing contractility, respiratory rate and stroke volume to drop while the tidal volume increases slightly, but remains essentially constant. For this reason the pacing rate is lowered until time 10, when contractility and stroke volume return to their normal values. Since the tidal volume and the instantaneous respiratory rate are still falling, the pacing rate continues decreasing. At times 11 and 12 as the respiratory rate and tidal volume decrease more slowly, the pacing rate is accordingly changed until the quiescent value according to the long term average of the respiratory rate of the individual patient is reached at time 14.

This invention has provided methods for automatic dynamic control of pacing rate for use in pacemakers so that the individual characteristics of patient's are reflected accurately for optimizing the heartbeat rate over wide ranges of dynamic exercise and physiological activity ranges taking into account both instantaneous response necessity and the basic individual physiological condition of the patient. Yet a simple and easily administered control method has resulted that is readily adapted to rate controlled pacemaker systems of the present state of the art.

It has been ascertained in experiments with healthy persons that the pacing rate reached in this manner correlates very well with the heartbeat rates of healthy persons.

Figure 7:
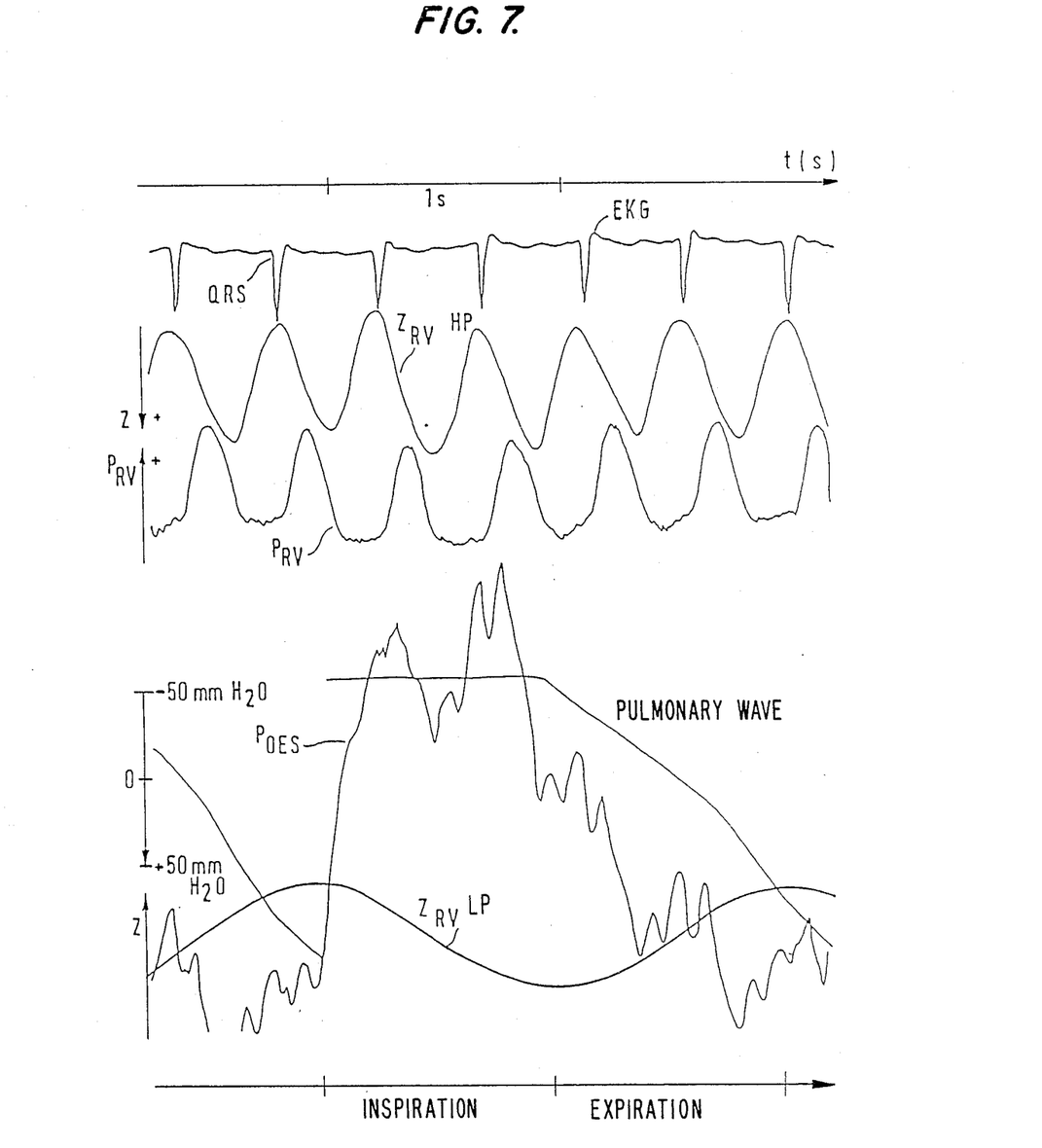
FIG. 7 is a waveform diagram comparing over a range of pulmonary activity various dynamic signals sensed in a patient.

More information on how the actual intracardiac signals are obtained, processed and weighted and how they correlate to other physiological parameters is shown in FIG. 7. Thus, the raw impedance signal is split into a high passed cardiac upper portion and a low passed pulmonary lower portion. In the cardiac signals, the increase of impedance Z due to stroke volume can be clearly recognized by a simultaneous increase of pressure in the right ventricle $P_{RV}$ with each cardiac action (QRS).

The inhalation or inspiration phase is associated with a drop of pressure in the esophagus $P_{OES}$ as a representative value of intrathoracic pressure, and the exhalation phase with a pressure increase over zero pressure transmission to the right heart causes, due to inhalation, the corresponding greater abundance of blood in the heart and thus an inspiratorily lower impedance $Z_{TV}$ LP.

Figure 8:
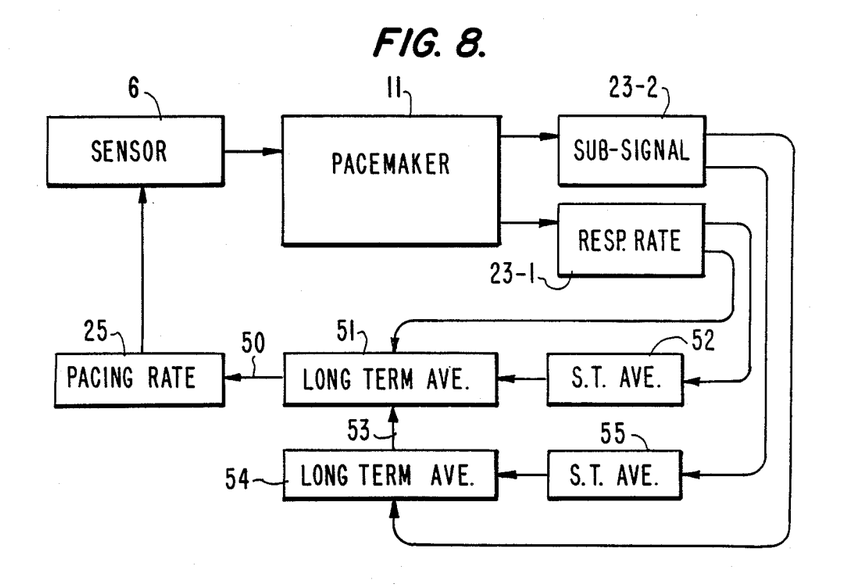
FIG. 8 is a block flow diagram illustrating the algorithmic relationship for automatic control of a pacemaker pacing rate from dynamically sensed signals to match the individual characteristics of a patient over a significant range of physiological activity changes in accordance with the teachings of this invention.

In FIG. 8 the hereinbeforedescribed method of pacing rate control afforded by this invention providing improved algorithmic control of pacing rate from sensed dynamic signals representative of the physiological activities of a pacemaker patient is shown in flow diagram form as related to the pacemaker of FIG. 2.

Thus, the pacing rate is established at 25 in response to the pacing rate control signal at 50 which is derived as a basic function of the long term average 51 of the respiratory rate signal 32-1 representing patient's basic cardiopulmonary condition. It additionally gets modified by its short term average 52. The pacing rate control signal is further controlled by one or more sub-signals 23-2 and the like in an appropriate functional relationship 53 to the base control signal, namely the modulated long term averaged response rate signal at 51. The subsignals are similarly developed with a long term averaged base characteristic 54 modified by an appropriate functional relationship of the short term subsignal instantaneous component average 55. By appropriate selection of the time constants of 54 and 55 a physiological suitable ramp back characteristic of those signals can be achieved. It is a further feature of this invention to make the influence of 54 and 55 to rate control a function of the patient's condition which is recognized by the value 51. This means that 53 becomes a function of 51 as well as the effect of 52 on 51 becomes a function of 52.

It is evident therefore that this invention provides novel and improved sensing and pacing control means and methods including specifically improved ventilation control of rate responsive cardiac pacemakers. Thus, tailored control of pacing rates to meet the personal attributes and needs of the patient in a simplified installation with a choice of control algorithms now is made feasible. Having therefore advanced the state of the art, those features of novelty typical of spirit and nature of the invention are defined with particularity in the following claims.

I claim:
1. The method of relating the pacing rate for a patient's heartbeat comprising the steps of:
producing in response to activity of the patient at least one on-line real-time signal sensed by monitoring the dynamic activity of the patient,
developing from said signal a long term average indicating the condition of the patient representative of the patient's basic cardiopulmonary condition,
establishing a basic base line characteristic relationship to the long term average from said signal as the primary pacing signal for control of the patient's heartbeat,
establishing a short term average from the real-time signal representative of the patient's instantaneous cardiopulmonary condition,
varying the base line characteristic upward and downward as a function of the short term average to produce a dynamically modified pacing control signal incorporating both said long term average and said short term average, and
pacing the patient's heartbeat as a function of the dynamically modified pacing control signal.

2. The method of claim 1 with the further steps of:
deriving from said on-line signal a signal representing a long term average of the patient's tidal volume representing his individual basic cardiopulmonary condition as said long term average, and
deriving from said on-line signal a signal representing a short term average of the patient's tidal volume as said short term average representing the instantaeous cardiopulmonary condition of the patient.
varying the basic tidal volume signal as a function of the short term average of the tidal volume signal to establish a tidal volume control signal, and varying the pacing control signal as a function of the tidal volume control signal.

3. The method of claim 1 with the further steps of:
producing from the cardiovascular system of the patient an on-line real-time cardiac signal representative of the patient's cardiac activity,
deriving from the cardiac signal a long term average representing the patient's basic cardiac condition as a basic cardiac signal,
deriving from said cardiac signal term average as an instantaneous cardiac signal representing the patient's instantaneous cardiac condition,
varying the basic cardiac signal as a function of the instantaneous cardiac signal to derive a cardiac control signal, and
varying the dynamically modified pacing control signal additionally as a function of the cardiac control signal.

4. The method of claim 1 with the further steps of:
producing in response to the physical activity of the patient a further activity signal representative of the level of further physical activity of the patient,
developing a long term average of the further activity signal to produce a basic further activity signal representative of the basic level of physical activity of the patient,
developing a short term average of the further activity signal to produce an instantaneous activity signal representative of the instantaneous further physical activity of the patient,
varying the basic further activity signal as a function of the instantaneous further activity signal to provide a further activity control signal, and
varying the dynamically modified pacing control signal further as a function of the further activity control signal.

5. The method of claim 1 with the further steps of:
producing in response to physical activity of the patient a further activity signal representative of the level of further physical activity of the patient, and
varying the dynamically modified pacing control signal additionally as a function of the further activity signal.

6. The method of controlling the pacing rate of a patient wearing a pacemaker comprising the steps of:
isolating at least one on-line real-time activity signal from the cardiovascular-pulmonary system of a patient representative of a physiological activity variably related to the change of heartbeat rate in a normal person,
developing a base line charteristic from a long term average of said activity signal.,
developing an instantaneous activity signal from a short term average of the activity signal,
varying the base line characteristic upward and downward dynamically to produce a modified long term average as a function of the instantaneous activity signal to produce a pacing control signal, and
pacing the heart at a rate controlled by the pacing control signal.

7. A heart pacemaker comprising in combination, pulse generator means for producing pacing pulses, means for measuring at least one parameter varying with physiological activity of a patient representative of dynamically changing physiological activity and individual characteristics of the patient relating to pacing rate, means responsive to the measured parameter for obtaining and averaging measured data relating to pacing rate over a predetermined long term period and establishing therefrom a base line characteristic, means for modifying the base line characteristic upward and downward dynamically with a short term average of a measured parameter to account for instantaneous dynamic changes for producing a pacing control signal incorporating dynamic changes in pacing rates, and means for controlling the pacing rate of the patient as a function of the dynamically modified base line characteristic of the pacing control signal.

8. The pacemaker of claim 7 wherein said parameter is the respiratory rate of the patient.

9. The pacemaker of claim 7 including means for further modifying the base line characteristic by a sub-signal of a different parameter related to the patient's physiological activity.

10. The pacemaker of claim 7 wherein said parameter is related to the pulmonary activity of the patient.

11. The pacemaker of claim 7 wherein said parameter is related to the cardiac activity of the patient.

12. The method of regulating the pacing rate for a patient's heartbeat comprising the steps of:
producing from a patient an on-line real-time dynamic physiological activity signal representative of a condition relating to the heartbeat rate,
producing a long term average of said physiological activity signal,
establishing from the long term average a pacing function having a substantially linear relationship with the heartbeat rate with a predetermined slope,
producing a short term upward and downward variation from said pacing function in response to a parameter of the activity signal, and
pacing the patient's heart at a rate corresponding to a combination of short term variation and said pacing function thereby to produce a smooth transition in pacing rate when exercise is encountered and terminated.

13. Pacemaker apparatus for regulating the pacing rate of a patient comprising in combination:
sensing means for deriving from the patient an on-line real-line time dynamic physiological activity signal representative of a condition related to the heartbeat rate,
processing means for producing a long term average pacing function of said signal having a sunstantially linear relationship with the heartbeat rate of a predetermined slope,
means for producing a short term upward and downward variation from said pacing function in response to a parameter of the activity signal, and
means for establishing a pacing rate in response to a combination of said pacing function and the short term variation thereby to produce a smooth transition in pacing rate when exercise is encountered and termination.

14. The method of heart pacing comprising the steps of:
monitoring at least one physiological parameter indicative of the metabolic condition of a patient,
establishing a long term averaged value from said parameter indicative of an individual patient's condition,
formulating from said averaged value a primary functional relationship for control of the pacing rate of an individual patient,
deriving an instantaneous physiological change in the patient's condition induced by exercise that varies as a function of the patient's individual need for variation in pacing rate from said primary functional relationship, and
controlling the pacing rate of the patient in response to a basic pacing control algorithm superimposing dynamic variations in the instantaneous changes upon the primary functional relationship to derive a modified dynamic function of the long term average value.

15. The method of heart pacing comprising the steps of:
monitoring at least one physiological parameter indicative of the metabolic condition of a patient,
establishing a long term function of said monitored parameter indicative of an individual patient's condition,
formulating from said long term function a base line pacing control signal,
establishing a dynamic short term signal indicative of a patient's metabolic condition,
modifying the base line pacing control signal upward and downward dynamically as a function of said dynamic short term signal to establish a new dynamically varying base line for the pacing control signal, and
controlling the pacing rate of the patient as a function of the base line pacing control signal with the new dynamically varying base line.

16. Apparatus for pacing the heartbeat of a patient, comprising in combination:
measuring means for monitoring at least one physiological parameter indicative of the metabolic condition of a patient,
means for establishing a long term base line function from the monitored parameter,
means for dynamically modifying the base line function upward and downward with short term changes derived from the parameter being monitored,
and means for controlling the pacing rate of the patient from the dynamically modified long term baseline function.

* * * * *